United States Patent
Schwiening

(10) Patent No.: US 9,597,038 B2
(45) Date of Patent: Mar. 21, 2017

(54) APPARATUS FOR MONITORING A SUBJECT DURING EXERCISE

(75) Inventor: Christof Schwiening, Cambridge (GB)

(73) Assignee: CAMBRIDGE ENTERPRISE LIMITED, Cambridge Cambridgeshire (GB)

( * ) Notice: Subject to any disclaimer, the term of this patent is extended or adjusted under 35 U.S.C. 154(b) by 58 days.

(21) Appl. No.: 14/003,500

(22) PCT Filed: Mar. 7, 2012

(86) PCT No.: PCT/GB2012/050503
§ 371 (c)(1),
(2), (4) Date: Feb. 11, 2014

(87) PCT Pub. No.: WO2012/120298
PCT Pub. Date: Sep. 13, 2012

(65) Prior Publication Data
US 2014/0323820 A1  Oct. 30, 2014

(30) Foreign Application Priority Data
Mar. 8, 2011 (GB) .................................. 1103921.1

(51) Int. Cl.
*A61B 5/0205* (2006.01)
*A61B 5/00* (2006.01)
(Continued)

(52) U.S. Cl.
CPC .............. *A61B 5/7278* (2013.01); *A61B 5/01* (2013.01); *A61B 5/0205* (2013.01);
(Continued)

(58) Field of Classification Search
None
See application file for complete search history.

(56) References Cited

U.S. PATENT DOCUMENTS 4,658,832 A * 4/1987 Brugnoli .............. A61B 5/0002
340/870.09
4,981,681 A * 1/1991 Tosti .................... A61K 9/0014
424/78.05
(Continued)

FOREIGN PATENT DOCUMENTS

IE   WO 2005098467 A2 * 10/2005 ........... A61B 5/1112
WO      2005/098467 A2   10/2005

OTHER PUBLICATIONS

C.T.M. Davies, Thermoregulation During Exercise in Relation to Sex and Age, Eur. J. Appl. Physiol. 42, 71-79 (1979).*
(Continued)

*Primary Examiner* — William Thomson
*Assistant Examiner* — Manolis Pahakis
(74) *Attorney, Agent, or Firm* — Kilpatrick Townsend & Stockton LLP

(57) ABSTRACT

Apparatus for determining maximal oxygen uptake per unit time for a subject. The apparatus comprises at least one body sensor measuring body temperature of the subject; at least one body sensor measuring sweat output of the subject; and a processor. The processor is configured to receive measurements from said at least one body sensors; determine whether said subject is exercising in steady state; and calculate, subject to said determining, maximal oxygen uptake per unit time for said subject using said received measurements.

10 Claims, 12 Drawing Sheets

(51) Int. Cl.
   A61B 5/01    (2006.01)
   A61B 5/083   (2006.01)
   A61B 5/11    (2006.01)
(52) U.S. Cl.
   CPC ........ *A61B 5/02055* (2013.01); *A61B 5/0833* (2013.01); *A61B 5/1118* (2013.01); *A61B 5/4266* (2013.01); *A61B 5/6824* (2013.01); *A61B 5/7275* (2013.01); *A61B 2503/10* (2013.01)

(56) References Cited

U.S. PATENT DOCUMENTS

| | | | | |
|---|---|---|---|---|
| 4,981,687 | A * | 1/1991 | Fregly | A23L 2/38 424/439 |
| 7,052,472 | B1 * | 5/2006 | Miller | A61B 5/01 600/549 |
| 8,961,415 | B2 * | 2/2015 | LeBoeuf | A61B 5/00 600/301 |
| 2003/0013072 | A1 * | 1/2003 | Thomas | 434/247 |
| 2003/0212315 | A1 * | 11/2003 | Wiesmann | A61B 5/14551 600/322 |
| 2004/0039254 | A1 * | 2/2004 | Stivoric | A61B 5/0205 600/300 |
| 2005/0026123 | A1 * | 2/2005 | Raniere | A63B 24/0062 434/247 |
| 2006/0063980 | A1 * | 3/2006 | Hwang | A61B 5/222 600/300 |
| 2007/0239038 | A1 * | 10/2007 | Nicolaescu | A61B 5/01 600/483 |
| 2009/0082677 | A1 * | 3/2009 | Shih | A61B 5/01 600/485 |
| 2009/0157327 | A1 * | 6/2009 | Nissila | A61B 5/6831 702/19 |
| 2009/0270743 | A1 * | 10/2009 | Dugan | A61B 5/0002 600/500 |
| 2010/0033303 | A1 * | 2/2010 | Dugan | A61B 5/0002 340/5.82 |
| 2010/0249619 | A1 * | 9/2010 | Kasama | A61B 5/02416 600/502 |

OTHER PUBLICATIONS

Greenhaff P.L., Cardiovascular fitness and thermoregulation during prolonged exercise in man, Br. J. Sp. Med; vol. 23, 1989.*
Gonzalez et al., Expanded prediction equations of human sweat loss and water needs, J Appl Physiol 107: 379-388, 2009.*
Withers P.C., Measurement of VO2, VCO2 and evaporative water loss with a flow-through mask, 1977.*
Yoshida et al., Effect of aerobic capacity on sweat rate and fluid intake during outdoor exercise in the heat, Eur J Appl Physiol (1995) 71:235 239.*
Montain et al., Control of thermoregulatory sweating is altered by hydration level and exercise intensity, J Appl Physiol Nov. 1995;79(5):1434-9.*
McMurray et al., Thermoregulation in swimmers and runners, Journal of Applied Physiology 1979 vol. 46 No. 6, 1086-1092.*
Amorim et al., Is sweat rate during steady state exercise related to maximum oxygen uptake?, Journal of Thermal Biology 31 (2006) 521-525.*
Kondo et al., Regional differences in the effect of exercise intensity on thermoregulatory sweating and cutaneous vasodilation, Acta Physiol Scand 1998, 164, 71-78.*
International Preliminary Report on Patentability mailed Sep. 19, 2013, from PCT Application No. PCT/GB/2012/050503 (8 pages).
Examination Report mailed Jun. 16, 2014, from European Application No. 12709157.7 (6 pages).
Havenith et al., "The relative influence of physical fitness, acclimatization state, anthropometric measures and gender on individual reactions to heat stress," Database Medline, US National Library of Medicine, Database accession No. NLM2079061 abstract (European Journal of Applied Physiology and Occupational Physiology, 1990, vol. 61, No. 5-6, pp. 419-427).
Ichinose-Kuwahara et al., "Sex differences in the effects of physical training on sweat gland responses during a graded exercise," Experimental Physiology, Aug. 2010, vol. 95, No. 10, pp. 1026-1032.
Schwiening et al., "Absolute power, not sex, promotes perspiration," Experimental Physiology, Apr. 2011, vol. 96, No. 5, pp. 556-558.
International Search Report and Written Opinion, mailed Jun. 18, 2012, PCT application No. PCT/GB2012/050503, 10 pages.
Benzinger, T.H., "On physical heat regulation and the sense of temperature in man," *PNAS*, 1959, pp. 645-659, vol. 45.
Fiala, D., Lomas, K.J., and Stohrer, M., "A computer model of human thermoregulation for a wide range of environmental conditions: the passive system," *Journal of Applied Physiology*, 1999, pp. 1957-1972, vol. 87(5).
Greenhaff, P.L., "Cardiovascular fitness and thermoregulation during prolonged exercise in man," *Br J Sp Med*, 1989, pp. 109-114, vol. 23(2). Butterworth & Co.
Havenith G. and Van Middendorp, H., "The relative influence of physical fitness, acclimatization state, anthropometric measures and gender on individual reactions to heat stress," *European of Journal Applied Physiology Occupational Physiology*, 1990, pp. 419-417, vol. 61.
Havenith, G., Luttikholt, V.G., and Vrijkotte, T.G., The relative influence of body characteristics on humid heat stress response, *European Journal of Applied Physiology Occupational Physiology*, 1995, pp. 270-279, vol. 70(3).
Kondo, N., Nishiyasu, T., Inoue, Y., Koga, S., "Non-thermal modification of heat-loss responses during exercise in humans," *European Journal of Applied Physiology*, 2010, pp. 447-458, vol. 110.
Saltin, B. and Hermansen, L., "Esophageal, rectal, and muscle temperatureduring exercise," *Journal of Applied Physiology*, 1966, pp. 1757-1762, vol. 21(6).
Shibasaki, M. and Crandall, C.G., "Mechanisms and controllers of eccrine sweating in humans," *Front Biosci*, 2011, pp. 685-696, vol. 2.
Yamazaki, F. et al., "Responses of sweating and body temperature to sinusoidal exercise in physically trained men," *Journal of Applied Physiology*, 1996, pp. 491-495, vol. 80(2).
Zhang, H., Huizenga, C., Arens, E. and Yu, T. "Considering individual physiological differences in a human thermal model," *Journal of TH*, 2001, pp. 401-408, vol. 26.

* cited by examiner

| Code | Age (years) | Sex | Height (m) | Weight (kg) | Spirometry (L min-1) | Anthropometric error | Sweating error | Anthropometric prediction | Sweating prediction |
|------|------|--------|------|------|------|------|------|------|------|
| AS | 47 | Female | 1.56 | 52.4 | 1.97 | -25% | -12% | 1.57 | 1.76 |
| KS | 34 | Female | 1.73 | 59 | 3.15 | 2% | 3% | 3.2 | 3.24 |
| GS | 16 | Female | 1.58 | 50 | 3.52 | -46% | 8% | 2.41 | 3.83 |
| MS | 14 | Male | 1.53 | 40 | 2.82 | -52% | -7% | 1.85 | 2.63 |
| RG | 76 | Male | 1.67 | 65 | 2.33 | -21% | -2% | 1.93 | 2.29 |
| EC | 20 | Male | 1.94 | 95 | 4.97 | 17% | 5% | 5.96 | 5.21 |
| HD | 48 | Male | 1.9 | 91.5 | 3.44 | 30% | 9% | 4.9 | 3.8 |
| RA | 33 | Male | 1.92 | 79 | 5.91 | -17% | 7% | 5.04 | 6.35 |
| EM | 18 | Male | 1.87 | 83.5 | 4.61 | 12% | -6% | 5.22 | 4.33 |

Fig 11

APPARATUS FOR MONITORING A SUBJECT DURING EXERCISE

This application is a U.S. National Phase application under 35 USC 371 of PCT Application No. PCT/GB2012/050503 filed Mar. 7, 2012, which claims priority to GB Patent Application No. 1103921.1, filed Mar. 8, 2011, the disclosures of which are incorporated by reference herein.

TECHNICAL FIELD

The invention relates to methods and apparatus for monitoring the performance of a person undertaking exercise, in particular, by calculating $\dot{V}O_2$ max, the maximal oxygen uptake per unit time.

BACKGROUND ART

Thermoregulatory sweating is well known to depend upon core body temperature (e.g. Benzinger, T. H. 1959 On physical heat regulation and the sense of temperature in Man. PNAS 45, 645-659). However, its precise control during exercise has proved difficult to quantify (see Kondo N., Nishiyasu, T., Inoue, Y., Koga, S. 2010. Non-thermal modification of heat-loss responses during exercise in humans. Eur J Appl Physiol 110, 447-458 for a recent review). Early work (Saltin, B. and Hermansen, L. 1966. Esophageal, rectal, and muscle temperature during exercise. J Appl Physiol 21(6) 1757-1762) showed that body temperature rose in proportion to an individual's capacity to do work, whilst sweating rose in proportion to the absolute work rate. However, Saltin & Hermansen (1966) provided no means by which these measurements might be combined to reveal $\dot{V}O_2$ max.

Subsequent researchers investigated these two relationships in more detail demonstrating the importance of $\dot{V}O_2$ max in determining the relationship between body temperature and sweating. One publication (Greenhaff, P. L. 1989. Cardiovascular fitness and thermoregulation during prolonged exercise in man. Br J Sports Med 23(2) 109-114) suggested 55% of the sweat loss could be accounted for by $\dot{V}O_2$ max and another publication (Havenith, G. and van Middendorp, H. 1990. The relative influence of physical fitness, acclimatization state, anthropometric measures and gender on individual reactions to heat stress. Eur J Appl Physiol Occup Physiol 61(5-6) 419-427) showed the importance of many other parameters including body fat, surface area and acclimation.

These complexities result in various computational models of thermoregulation that do not allow for a simple derivation of $\dot{V}O_2$ max from physiological parameters (see Havenith, G., Luttikholt, V. G. and Vrijkotte, T. G. 1995. The relative influence of body characteristics on humid heat stress response. Eur J Appl Physiol Occup Physiol 70(3) 270-279; Fiala, D., Lomas, K. J. and Stohrer, M. 1999. A computer model of human thermoregulation for a wide range of environmental conditions: the passive system. J Appl Physiol 87(5) 1957-1972; and Zhang, H., Huizenga, C., Arens, E. and Yu, T. 2001. Considering individual physiological differences in a human thermal model. Journal of Th 26 401-408). Indeed, non-thermal modulation of sweating would appear to rule out a simple relationship between sweating and body temperature that was dependent upon $\dot{V}O_2$ max alone (see Yamazaki, F. et al. 1996. Responses of sweating and body temperature to sinusoidal exercise in physically trained men. J. Appl. Physiol., 80(2), 491-495; Shibasaki, M. and Crandall, C. G. 2011. Mechanisms and controllers of eccrine sweating in humans. Front. Biosci. 2, 685-696).

Methods and apparatus for either estimating or calculating $\dot{V}O_2$ max (defined as the maximal oxygen uptake per unit time) are known. $\dot{V}O_2$ max may also be known as maximal oxygen consumption rate, peak oxygen uptake or aerobic capacity and is the maximum capacity of an individual's body to transport and use oxygen during exercise. The name is derived from $\dot{V}$ which represents volume per time and $O_2$ representing oxygen. The dot above the V denotes rate of ventilation. $\dot{V}O_2$ max can be defined either as the maximal oxygen uptake per unit time (ml min$^{-1}$) or it can be expressed per unit body mass (ml min$^{-1}$ kg$^{-1}$). The ml min$^{-1}$ definition is useful when considering absolute power output of an individual whereas the ml min$^{-1}$ kg$^{-1}$ is usually used when considering an individual's potential athletic ability. It is possible to provide an estimate of an individuals $\dot{V}O_2$ max without performing any exercise testing using anthropometric data (e.g. an individual's weight, age, height, sex and amount of body fat). However, these estimates have limited accuracy since they do not take into account the effects of training and other physiological differences (e.g. heart disease). It is possible to improve anthropometric estimates of $\dot{V}O_2$ max using estimates of training (e.g. questionnaires concerning the intensity and duration of exercise) but, such techniques both rely on accurate knowledge of an individual's training and assume a standard training effect of the reported exercise intensity on $\dot{V}O_2$ max.

The known methods calculate $\dot{V}O_2$ max from spirometry and measurements of oxygen concentration during ramped increases in exercise intensity to exhaustion. There are two classes of indirect assessments of $\dot{V}O_2$ max, either using spirometry and oxygen measurements at non-maximal intensities followed by extrapolation to a theoretical maximum or by performance on one of many exercise tests (e.g. Cooper $\dot{V}O_2$ max test, Astrand treadmill test).

Whilst spirometry with oxygen measurement during maximal exertion is, by definition, the only true way that $\dot{V}O_2$ max can be determined it presents several major problems. First, the equipment to measure oxygen concentrations is expensive and requires careful maintenance since it directly interferes with breathing during a period of intense stress on the ventilatory system. The facemasks and tubes used make the test unpleasant and can restrict performance. Second, maximal exertion is required. Whilst maximal efforts can be obtained from experienced athletes the test is not suitable for the general population or those with health disorders where such intense efforts are not well tolerated, or may even be undesirable.

Exercise performance assessments of $\dot{V}O_2$ max are equally problematic since they too require maximal exertion and the estimate of $\dot{V}O_2$ max will depend upon the modality of the exercise chosen and the efficiency of the individual at that particular modality (e.g. an efficient runner with a low $\dot{V}O_2$ max may obtain a similar assessment as an inefficient runner with a $\dot{V}O_2$ max). Thus, an exercise performance $\dot{V}O_2$ max assessment is limited in its usefulness since it does not differentiate between poor circulatory performance or poor technique.

Despite the difficulties identified above, $\dot{V}O_2$ max testing is a popular means to measure cardiovascular fitness. The present invention recognises the need for an improved technique for assessing $\dot{V}O_2$ max which is suitable for all users.

STATEMENTS OF INVENTION

According to a first aspect of the invention, there is provided apparatus for determining cardiovascular fitness of a subject by determining maximal oxygen uptake per unit time for said subject, the apparatus comprising
  at least one body sensor measuring body temperature of the subject;
  at least one body sensor measuring sweat output of the subject; and
  a processor configured to
  receive measurements from said at least one body sensors;
  determine whether said subject is exercising in steady state; and
  calculate, subject to said determining, maximal oxygen uptake per unit time for said subject using said received measurements.

According to a second aspect of the invention, there is provided a method for determining cardiovascular fitness of a subject by determining maximal oxygen uptake per unit time for said subject, the method comprising
  measuring body temperature of the subject;
  measuring sweat output of the subject;
  determine whether said subject is exercising in steady state; and
  calculate, subject to said determining, maximal oxygen uptake per unit time for said subject using measurements of body temperature and sweat output from said measuring steps.

The method is preferably computer-implemented with calculations occurring in a processor or similar device.

The present applicant has recognised that the non-steady state nature of the measurements and models of the prior art has obscured a simple relationship. The fundamental basis of the test is the measurement of two primary parameters during steady-state exercise—body temperature and sweating rate.

Maximal oxygen uptake per unit time $\dot{V}O_2$ max) may also be known as maximal oxygen consumption rate, peak oxygen uptake or aerobic capacity and is the maximum capacity of an individual's body to transport and use oxygen during exercise. Accordingly, the invention may be considered to be calculating an indication of the training undertaken by an individual and thus the calculation of maximal oxygen uptake per unit time may be a simple calculation which may be termed a training index.

The following features apply equally to both aspects.

The measurement of several other parameters, including heart rate, age, height, weight and environmental conditions may allow a greater degree of accuracy. Accordingly, there may be least one room sensor measuring parameters of a room in which the subject is exercising and/or at least one additional body sensor measuring other parameters, e.g. the heart rate, of the subject. Said processor may be configured to receive measurements from said at least one room and body sensor and to use one or both of said measurements when determining whether said subject is exercising in steady state. Said measurements from said at least one room sensor and/or said at least one additional body sensor may also be used to calibrate one or more measurements from said at least one body sensors.

The at least one body sensor may comprise at least one sensor measuring skin temperature and at least one sensor measuring core temperature. A skin thermocouple may be used to measure skin temperature. A tympanic membrane device may be used to measure core temperature.

The at least one body sensor measuring sweat output may be in the form of a ventilated air-tight sleeve impervious to water which may allow the collection of sweat from a large known area of skin. The sleeve may be connected to an air circulating system. The sweat output may be measured by a drying balance and/or by measuring humidity and air flow through the air circulating system containing a drying agent.

The evidence to support the possibility of extracting $\dot{V}O_2$ max from sweating and body temperature is derived from the data in Ichinose-Kuwahara, T., Inoue, Y., Iseki, Y., Hara, S., Ogura, Y. and Kondo, N. 2010. Sex differences in the effects of physical training on sweat gland responses during a graded exercise. Exp Physiol 95(10) 1026-1032. The simplification made in this paper relative to the other prior art was to perform exercise in steady-state conditions. This removes the dynamic components of the temperature-sweating relationship present in previous studies. Whilst there is no such conclusion in Ichinose-Kuwahara, the present applicant has determined that by reanalyzing the data shows, that $\dot{V}O_2$ max alone can explain the temperature-sweating relationship for several different experimental groups.

The function (linear or non-linear) for calculating maximal oxygen uptake per unit time from sweat output and temperature may be determined from a combination of a sweating relationship relating sweat output to work rate and a temperature relationship relating body temperature to work rate with said combination producing a relationship between sweat output and body temperature which is dependent on one variable, namely maximal oxygen uptake per unit time.

Sweating is a simple, although potentially non-linear, function of absolute work rate. Determining the sweating relationship may be done by defining the relationship as $SO_{calculated} = F(\dot{V}O_2, constants)$ where $SO_{calculated}$ is the calculated sweat output, F is a function, $\dot{V}O_2$ is representative of absolute work rate, and adjusting the constants to fit the calculated sweat output to the measured sweat output. This may allow one to derive a single equation to relate these two parameters for a given set of environmental conditions (e.g. equation 4 in the detailed description). This equation will hold true, under steady-state conditions, for all people regardless of training, acclimation, weight or sex.

The observation that sweat production is related to absolute work rate is not new. (see Davies CTM (1979) Thermoregulation during exercise in relation to sex and age. Eur J Appl Physiol 42, 71-79.) Davies measured sweating in men and women, athletes and non-athletes during exercise. He concluded that there were no apparent sex differences in thermoregulatory function, and that maximum sweating rates were linearly related to $\dot{V}O_2$ max.

Another equation can be generated relating body temperature and relative work rate (see equation 1 below). As above for the sweating relationship, the temperature relationship may be determined by defining the relationship as $temp_{calcualted} = F(\%\dot{V}O_2 \text{ max}, constants)$ where $temp_{calculated}$ is the calculated temperature using the model, F is a function, $\%\dot{V}O_2$ max is representative of relative work rate, and adjusting the constants to fit the calculated temperature to the measured temperature. Again this equation, under steady-state conditions, holds true for the general population.

Relative work rate is the absolute work rate divided by the maximal work rate. By combining these equations one can produce the final equation that produces the relationship between sweat output and body temperature dependent upon one variable alone, $\dot{V}O_2$ max together with three constants. By simple rearrangement $\dot{V}O_2$ max can therefore be derived from steady-state measurements of sweating and body temperature.

The processor may be thus configured to calculate maximal oxygen uptake per unit time from a non-linear function of sweat output and temperature. Such a function may be expressed as $$\dot{V}O_2\text{max} = \ln\left(\frac{\text{sweat ouput } (\mu g \text{ gland}^{-1} \text{ min}^{-1})}{a}\right) \times \frac{c}{\text{mass} \times (\text{temperature} - b)}$$

where $\dot{V}O_2$ max is maximal oxygen uptake per unit time per unit body mass, mass is the mass of the subject and a, b, c are constants.

Alternatively, the processor may be configured to calculate maximal oxygen uptake per unit time from a linear function of sweat output and temperature. Such a relationship may be expressed as:

$$\dot{V}O_2\text{max} = \frac{c * sweatoutput}{mass * (temperature - b)}$$

where b and c are constants.

The processor may be configured to receive body parameter data for the subject and to include said data in the calculating step. The body parameter data (anthropometric data, e.g. height, weight and/or age) may be included in the linear and/or non-linear relationships to improve the calculation.

For example, the processor may be configured to calculate maximal oxygen uptake per unit time from $$\dot{V}O_2\text{max} = \frac{e \times Sweat^{2.18}}{(temp - f)} - a \times \text{age} + b \times \text{height} + c \times \text{weight} - d$$

where a, b, c, d, e and f are constants.

In the equation above, the sweat production divided by body temperature refines an anthropometric calculation of $\dot{V}O_2$ max. It is known that training raises $\dot{V}O_2$ max and thus sweat production divided by a function of body temperature reports an index of training. Accordingly, the processor may be configured to calculate maximal oxygen uptake per unit time from sweat production divided by a function of body temperature. This is a simplified version of the calculation which may in fact be calculating a training index rather than an accurate maximal oxygen uptake per unit time. The tracking of this training index may be useful to follow the progression of fitness of an individual without needing to calculate $\dot{V}O_2$ max.

Thus, according to another aspect of the invention, there is provided a computer-implemented method for determining a training index for a subject, the method comprising
inputting measurements of body temperature of the subject into a processor;
inputting measurements of sweat output of the subject into a processor;
determining whether said subject is exercising in steady state; and
calculating, subject to said determining, the training index for said subject using said measurements of body temperature and sweat output.

According to another aspect of the invention, there is provided apparatus for determining an index of training for a subject, the apparatus comprising
at least one body sensor measuring body temperature of the subject;
at least one body sensor measuring sweat output of the subject; and
a processor configured to
receive measurements from said at least one body sensors;
determine whether said subject is exercising in steady state; and
calculate, subject to said determining, an index of training for said subject using said received measurements.

Said index of training may be calculated from sweat production divided by a function of body temperature. It will be appreciated that these aspects of the invention may be combined with the appropriate features of the first two aspects.

In both the non-linear and linear relationships described above, the constants may be determined either in advance of the tests from measurements taken during exercise from subjects with known maximal oxygen uptake under defined environmental conditions or at the time of the test from multiple measurements from an individual at the time of the test. The constants may be determined for each function or relationship by fitting a least squares fit or similar iterative algorithm to drill down to the constants. For example, for the sweating relationship, a least squares fit requires S to be a minimum with respect to variations in the constants, i.e. the following is calculated.

$$S = \Sigma_{all\text{-}measurements}\lfloor (SO_{calculated}(VO2_{measure}) - SO_{measured}(VO2_{measure}))^2 \rfloor$$

where $SO_{calculated}$ is the sweat output calculated from the model using the measurements of $\dot{V}O_2$ which is representative of absolute work rate and $SO_{measured}$ is the sweat output associated with each measurement of $\dot{V}O_2$.

The invention further provides processor control code to implement the above-described systems and methods, for example on a general purpose computer system. The code is provided on a carrier such as a disk, CD- or DVD-ROM, programmed memory such as non-volatile memory (e.g. Flash) or read-only memory (Firmware). Code (and/or data) to implement embodiments of the invention may comprise source, object or executable code in a conventional programming language (interpreted or compiled) such as C, or assembly code. As the skilled person will appreciate such code and/or data may be distributed between a plurality of coupled components in communication with one another.

According to another aspect of the invention, there is provided use of the apparatus or method described above to predict the performance of a subject during exercise. The apparatus and/or method may be used to predict the general fitness and/or the cardiovascular fitness of a subject.

The non-maximal nature of the test would allow for measurements at regular intervals allowing for ongoing assessment of the efficacy of training programs. Accordingly, the apparatus and/or method may be used to adapt the training program to suit the particular subject. Thus, according to another aspect of the invention, there is provided use of the apparatus or method described above to monitor a training program.

The technique presented here is a derivation of $\dot{V}O_2$ max from simple physiological measurements at non-maximal workloads and without the need to measure or indirectly restrict ventilation. The technique allows for $\dot{V}O_2$ max assessment in individuals for whom maximal exertion is undesirable (e.g. untrained, elderly, ill, obese and young). Furthermore, it also allows for $\dot{V}O_2$ max to be estimated without inducing a 'training' effect which can occur during a maximal test. Thus, the test may be repeated at more frequent intervals than maximal tests to monitor the progression through a training program. Also, since the devices used are non-invasive and the test of lower intensity than a maximal test, the test may be performed under non-laboratory conditions without highly trained technicians.

In light of the advantages above, the test may be performed at sports centres, health clubs, local sports clubs, weight-loss clubs and at exercise classes for the elderly, sick or obese. Thus, according to another aspect of the invention, there is provided use of the apparatus or method described above to monitor general fitness/cardiovascular fitness of the subject during a weight-loss program. According to another aspect of the invention, there is provided use of the apparatus or method described above to guide and monitor a medical treatment plan for a subject.

It may also have utility for the identification of children with high $\dot{V}O_2$ max who may not have had previous exposure to endurance sports. Thus, according to another aspect of the invention, there is provided use of the apparatus or method described above to select children for an exercise/fitness training program.

BRIEF DESCRIPTION OF THE DRAWINGS

There will now be described by way of example only, embodiments of the invention with reference to the accompanying drawings, in which:

FIG. 9c is a graph of sweat rate against tympanic temperature for the male of FIG. 9a;

FIG. 11 is a table comparing two methods of predicting $\dot{V}O_2$ max

DETAILED DESCRIPTION OF THE DRAWINGS

Figure 1:
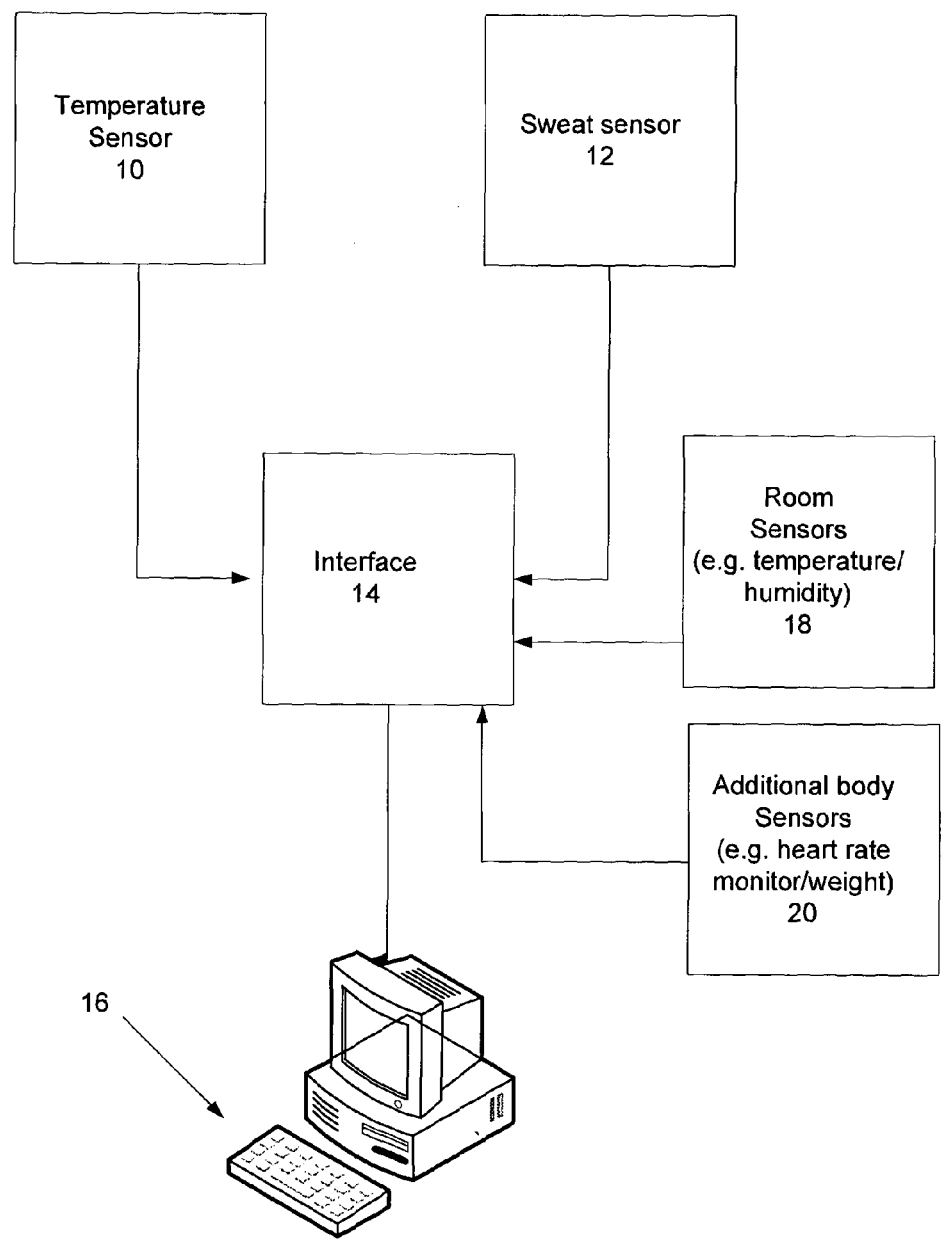
FIG. 1 is a schematic illustration of the components of the system.

FIG. 1 illustrates the components of the system. The two primary body parameters input to the system are body temperature measured by a temperature sensor 10 and a sweat monitoring sensor 12. The readings from these sensors are sent to an interface 14 which transmits the real-time data to a computer 16 (or other processor) for processing the data. The interface is preferably battery powered and enabled for wireless communication both with the sensors and the computer. This allows for greater portability. However, a mains powered and wired connection will also work. Providing a separate interface allows for the computer to be remotely located relative to the test subject and also allows for portability of the measuring instruments. However, it will also be appreciated that though the interface and computer are shown as separate components, the interface could be incorporated into the computer.

The term computer is intended to encompass any device with the capability to process the input data and may include a server, processor etc. The computer is configured to collect the data, analyse the data and to provide feedback either visually, e.g. via a display on the interface, via a monitor on the computer or verbally via an ear piece used by the subject.

The body temperature sensor may comprise one or more devices to take measurements on the surface of the skin, e.g. skin thermocouples, and one or more devices to take readings from the core. The surface temperature measurements may be combined with readings from the core in certain proportions.

Figure 3:
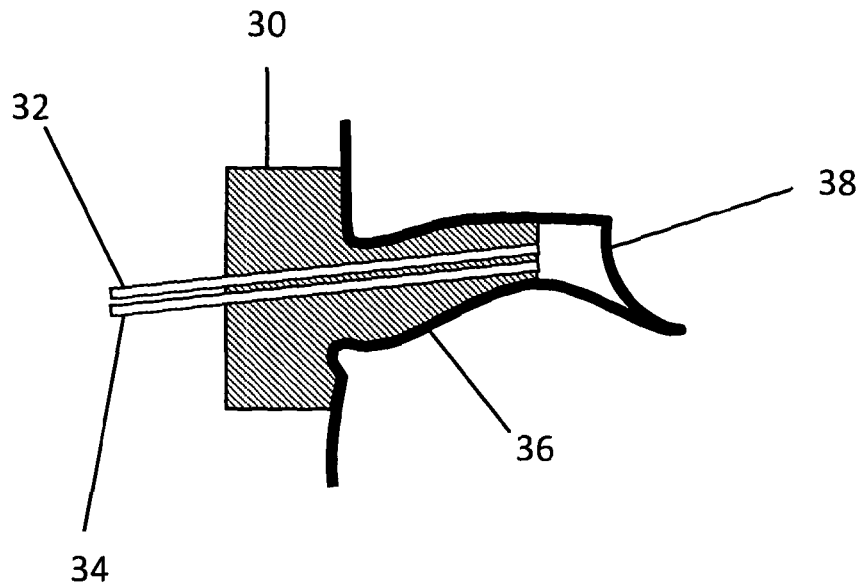
FIG. 3 is a schematic drawing of a temperature sensor which may be used with the system of FIG. 1.

FIG. 3 shows a device for measuring core temperature. The device is a continuous infrared tympanic temperature probe which works by detecting the infrared heat emission from the tympanic membrane. The device fits inside the external auditory canal 36 and points at the tympanic membrane 38. Correct positioning is important and thus the device may be combined with headphone output to ensure correct placing. As shown, the device comprises a replaceable ear plug 30 housing a hollow fibre 32 for auditory input and a fibre optic cable 34 for infra-red detection and measurement. The hollow fibre 32 connects to the headphone speaker and transmits sound to the tympanic membrane. The inclusion of the sound fibre allows the user to position the ear plug optimally. By positioning the ear plug for maximum volume the infra-red transmitting fibre will also become optimally placed for recording from the tympanic membrane. The fibre optic cable transmitting the infra-red radiation is connected to a temperature sensor module.

Alternatively, other known sensors may be used, e.g. oesophageal, rectal or orally consumed temperature sensitive transmitters. Tympanic infra-red measurement is perhaps the least invasive and has sufficient accuracy.

The sweat monitoring sensor may assess changes in sweating by assessing changes in whole body weight measurement. Alternatively, the sweat monitoring sensor may be one of many available devices for collecting and measuring evaporated or extruded sweat and is probably wearable. Local collection of sweat will require scaling dependent upon the location from which it is collected.

Figure 2A:
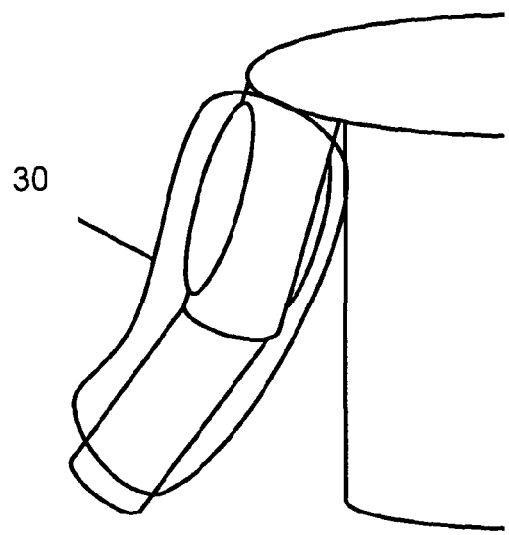
FIGS. 2a and 2b are schematic drawings of a sweating sensor which may be used with the system of FIG. 1.
Figure 2B:
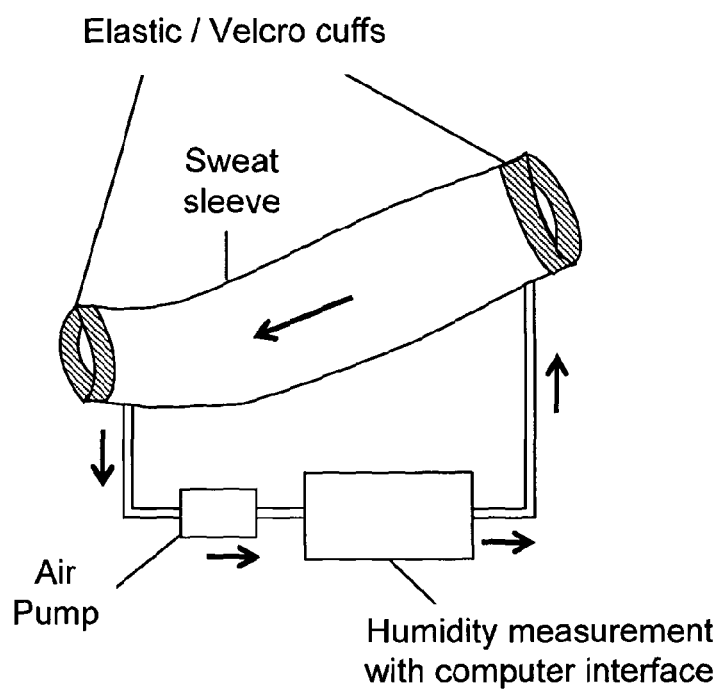

For illustrative purposes, FIGS. 2a and 2b show one such device in the form of a sweat sleeve 30. As shown in FIG. 2a, the sweat sleeve is placed over the arm of a user. The opposed ends of the air and water-tight sweat sleeve have elasticated or other similar means (e.g. fastening means such as Velcro™) to ensure a tight fit on (or seal around) a user's arm. The sweat sleeve is connected via tubing to an air pump and a mechanism, e.g. a drying balance, to measure the sweat collected. Sweat evaporates from the skin surrounded by the sleeve into the dry air that is pumped through the sleeve and is recovered from the air by the drying agent. The air is caused to circulate round the system under the control of an air pump. The air pump is controlled to change the speed of circulation to allow for a range of sweat production rates. Two in-line humidity sensors may also be incorporated in the tubing to improve the measurements. One downstream of the drying agent could report the need to replace the drying agent and one upstream could be used to calculate the sweat production. This sweat production can be calculated either by the change in humidity of a known volume of air per unit time, or more simply using the weight gain of the drying agent as reported by the drying balance.

As shown in FIG. 1, other sensors can be connected to the interface to provide real-time data to improve the output from the system. These sensors are optional and include room sensors 18 (such as room temperature and/or humidity sensors) and/or additional body sensors 20 (such as a heart rate monitor, body weight scales and/or an array device for measuring sweat gland density, e.g. using electrical conductance). For example, the data from these sensors can be used to assess when a user is working in steady-state exercise. Steady-state can be determined by using the rate of change of temperature, sweating or other physiological parameters. To achieve steady-state rapidly a protocol using an initially higher work load could be used. A simple technique would be the use of heart rate monitoring to set the exercise level at different stages in the test.

Figure 4A:
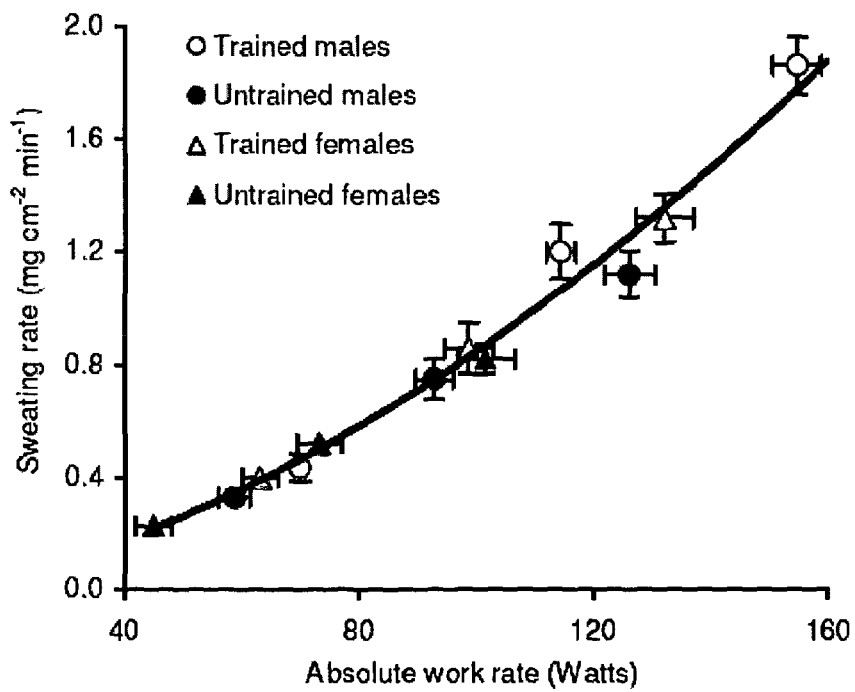
FIG. 4a is a graph plotting the data from Ichinose-Kuwahara et al. with sweating rate against absolute work rate.
Figure 4B:
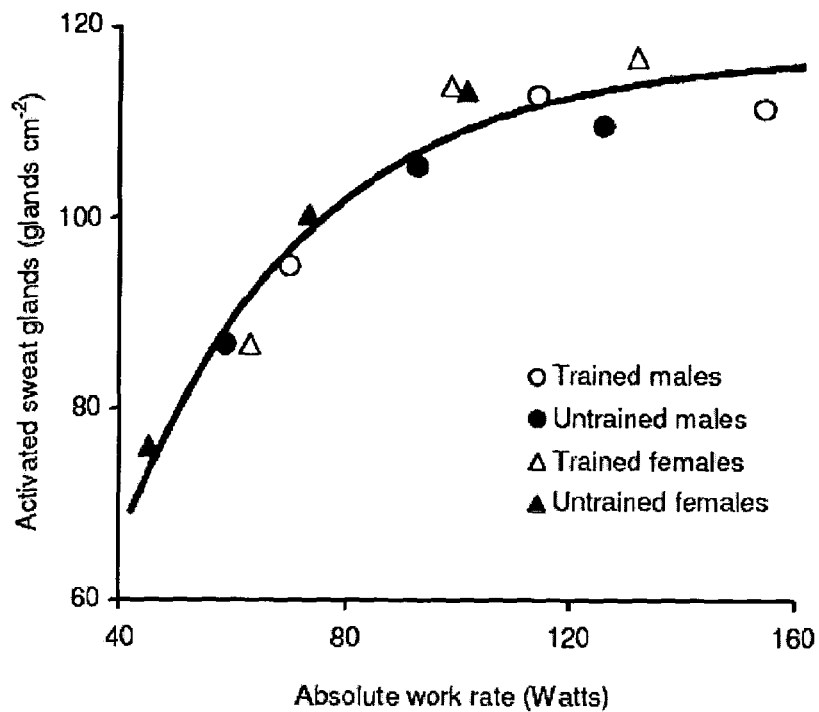
FIG. 4b is a graph plotting the data from Ichinose-Kuwahara et al. with the number of activated sweat glands per unit area of skin against absolute work rate.
Figure 4C:
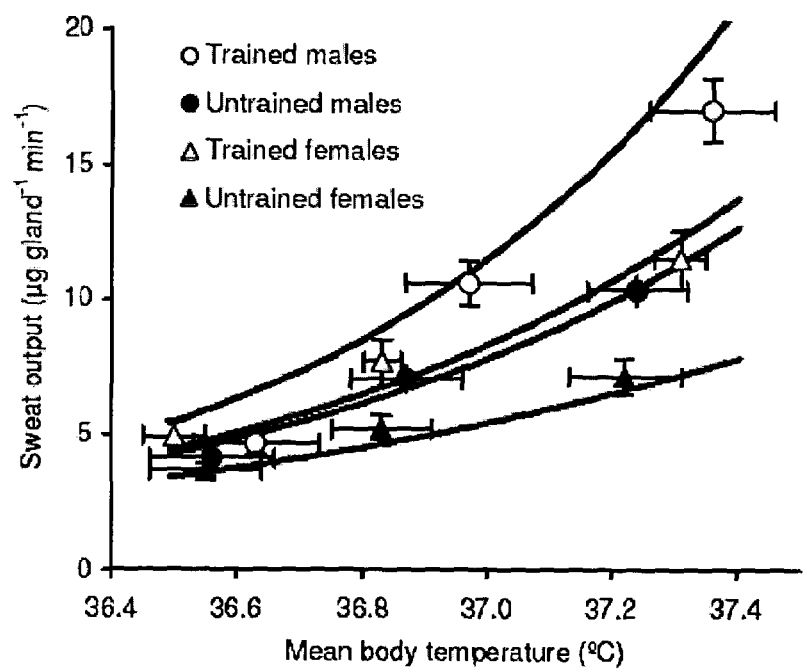
FIG. 4c is a graph plotting the data from Ichinose-Kuwahara et al. with sweat output per gland against temperature.

FIGS. 4a to 4c illustrate the theory behind the processing of the input data to determine $\dot{V}O_2$ max and its validation using data from a paper entitled "Sex differences in the effects of physical training on sweat gland responses during a graded exercise" by Ichinose-Kuwahara, T., Inoue, Y., Iseki, Y., Hara, S., Ogura, Y. and Kondo, N. published in 2010 by Exp Physiol 95(10) 1026-1032. The conclusions of Ichinose-Kuwahara et al. 2010 were drawn from plots of sweating responses in men and women at the same relative exercise intensity (%$\dot{V}O_2$ max). FIGS. 4a to 4c illustrate the data from Ichinose-Kuwahara et al. plotted with absolute rather than relative work rate on the x-axis.

In FIG. 4a, the mean sweating rates (±SEM) have been fitted with a power function of work rate: sweating rate (mg cm$^{-2}$ min$^-$))=0.0004 W$^{1.68}$. This function was obtained by performing a least squares fit of various non-linear functions to the dataset. This form of power function showed the best fit with the fewest parameters (two). There are other functions that fit. The precise nature of the function is likely to depend upon the efficiency of the heat loss by sweating. For example, if there is a lot of ineffective sweat loss by dripping rather than by evaporation, the function will be steeper. Furthermore, if the environmental temperature is low, radiant heat loss will make this relationship less steep at lower powers.

FIG. 4a reveals that the sweating rate can, apparently, be explained in its entirety by a single, simple function of absolute work rate without regard to either sex or training status. Since estimated body surface area is approx. 10% less in females, the estimated total sweat loss (L h$^{-1}$) against absolute power was also plotted. However, this did not expose any latent differences (data not shown).

FIG. 4b shows the mean number of activated sweat glands per unit area of skin against absolute work rate. The data points have been fitted with an exponential function of work rate (rate constant approx. 0.03 W$^{-1}$ and maximal activated sweat glands approx. 120 glands cm$^{-2}$). As with FIG. 4a, this function was obtained by performing a least squares fit of various non-linear functions to the dataset. In this case, a simple saturating exponential function is the best fit. The parameter of 120 gland cm$^{-2}$ will depend on the skin location selected. As with FIG. 4a, there does not appear to be any obvious sex or training effect. FIG. 4b suggests that all of the available sweat glands are active (male, female, trained or untrained) when the absolute work rate >100 W. This implies that any further increases in sweating rate in any group must come from a greater production from each gland.

FIG. 4c plots body temperature against sweating and shows that the data from all groups can be fitted by a single function using the maximum oxygen extraction reported for each group. Thus, the differences between the groups are entirely accounted for by $\dot{V}O_2$ max (ml min$^{-1}$) alone, without requiring any reference to sex or training status.

The function used to fit the data in FIG. 4c is derived as follows: Ichinose-Kuwahara et al. (2010) show in their FIG. 1 (bottom right) that mean body temperature rises linearly with %$\dot{V}O_2$ max, over the range 35% to 65%, with no significant differences identified between the four groups. Thus, mean body temperature, during exercise under their conditions, can be modelled by:

$$\text{Temperature} = \frac{2.4 \times \% \ \dot{V}O_2\text{max}}{100} + 35.7. \qquad \text{Equation 1}$$

The various constants (2.4 and 35.7) within the equation relating body temperature to relative exercise intensity (%$\dot{V}O_2$ max) can be derived from measurements on individuals with known $\dot{V}O_2$ max. The slope and intercept of this relationship are derived from individuals of known $\dot{V}O_2$ max under known environmental conditions by exercising them at different levels of intensity and measuring steady-state temperature. Using linear regression analysis, a range of appropriate values for given environmental conditions can be derived. Those given above are appropriate for calculation of $\dot{V}O_2$ max from the steady-state temperature at 30° C. and 45% humidity. Lower temperatures are desirable for convenient tests in the UK and will require an adjustment in constants to allow for the greater loss of heat via radiation.

Using the Table 1 data from Ichinose-Kuwahara et al. (2010), oxygen consumption (ml min$^{-1}$) can be calculated for each group at each relative workload using:

$$\dot{V}O_2 = \frac{\dot{V}O_2\text{max} \times \% \ \dot{V}O_2\text{max} \times \text{mass}}{100}. \qquad \text{Equation 2}$$

In other words, oxygen consumption ($\dot{V}O_2$ in ml min$^{-1}$) is equal to maximal oxygen uptake per unit time ($\dot{V}O_2$ max in ml min$^{-1}$ kg$^{-1}$) multiplied by the relative exercise intensity (%$\dot{V}O_2$ max) and mass (kg) divided by 100. Dividing both sides by the maximal oxygen uptake (also referred to as the maximal work rate) it can be seen that relative exercise intensity (also known as relative work rate) is simply the oxygen consumption (also known at the absolute work rate) divided by the maximal oxygen uptake.

In Ichinose-Kuwahara et al. (2010), FIG. 2 plots sweat output data against exercise intensity (i.e. against %$\dot{V}O_2$ max). In a similar manner to FIGS. 4a to 4c, this data is replotted showing sweat output data against $\dot{V}O_2$ (ml min$^{-1}$). As above, the function relating the parameters was obtained by performing a least squares fit of various non-linear functions to the dataset. In this case, a simple exponential function is the best fit i.e.

$$\text{sweat output (}\mu\text{g gland}^{-1}\text{ min}^{-1}) = 1.66 \times e^{\frac{\dot{V}O_2}{1018}}. \quad \text{Equation 3}$$

This is a rearrangement of the previous sweating rate plot but calculating sweating per gland rather than per cm$^2$ (i.e. taking into account the number of sweat gland per cm$^2$ activated).

As with previous functions in FIGS. 4a, 4b and 4c, equation 3 was obtained by defining a model to calculate sweat output ($SO_{calculated}$) from $\dot{V}O_2$ which is representative of absolute work rate, i.e.

$$SO_{calculated} = F(\dot{V}O_2, \text{constants}):$$

Where F is the function and the constants may be adjusted.

Thereafter, for each function to be tried, a least squares fit is applied to derive the relevant constants matching each function. A least squares fit requires S to be a minimum with respect to variations in the constants, i.e. the following is calculated.

$$S = \Sigma_{all\text{-}measurements}[(SO_{calculated}(VO2_{measure}) - SO_{measured}(VO2_{measure}))^2]$$

Where $SO_{measured}$ is the sweat output associated with each measurement of $\dot{V}O_2$.

Combining Equations 1, 2 & 3 it can be shown that:

$$\text{sweat output (}\mu\text{g gland}^{-1}\text{ min}^{-1}) = \quad \text{Equation 4}$$
$$1.66 \times e^{\frac{\dot{V}O_2 max \times mass \times (temperature - 35.7)}{2443}}.$$

This can be rearranged to shown that maximal oxygen uptake per unit time is a function of two time-varying parameters only, namely sweat output and body temperature. There is a third user dependent parameter, namely mass, but this is does vary over the time of the test.

$$\dot{V}O_2 max = \ln\left(\frac{\text{sweat output (}\mu\text{g gland}^{-1}\text{ min}^{-1})}{1.66}\right) \times \frac{2443}{mass \times (temperature - 35.7)}$$

As an alternative, the relationship between maximal oxygen uptake, sweat output and body temperature may a simple linear relationship, particularly in cool dry conditions. The relationship may be:

$$\dot{V}O_2 max = \frac{c * sweatoutput}{mass * (temperature - 35.7)}$$

In this relationship, $\dot{V}O_2$ max (ml min$^{-1}$ kg$^{-1}$) is proportional to sweat output and inversely proportional to mass and the temperature rise above the non-exercise resting temperature.

It is possible that the equations above will vary with environmental conditions and that some individuals might not fit into the relationship (e.g. those with sweat related disorders). The constants will certainly depend upon many factors (e.g. room temperature and humidity). It is also possible that the derived $\dot{V}O_2$ max may need adjusting for other factors, e.g. heat acclimation. It remains unclear within the literature as to the extent that heat acclimation can be accounted for by an increase in $\dot{V}O_2$ max. Similarly, the relationship may need calibrating to some extent for each individual. This can be achieved for some of the parameters by performing exercise at different workloads.

Figure 5:
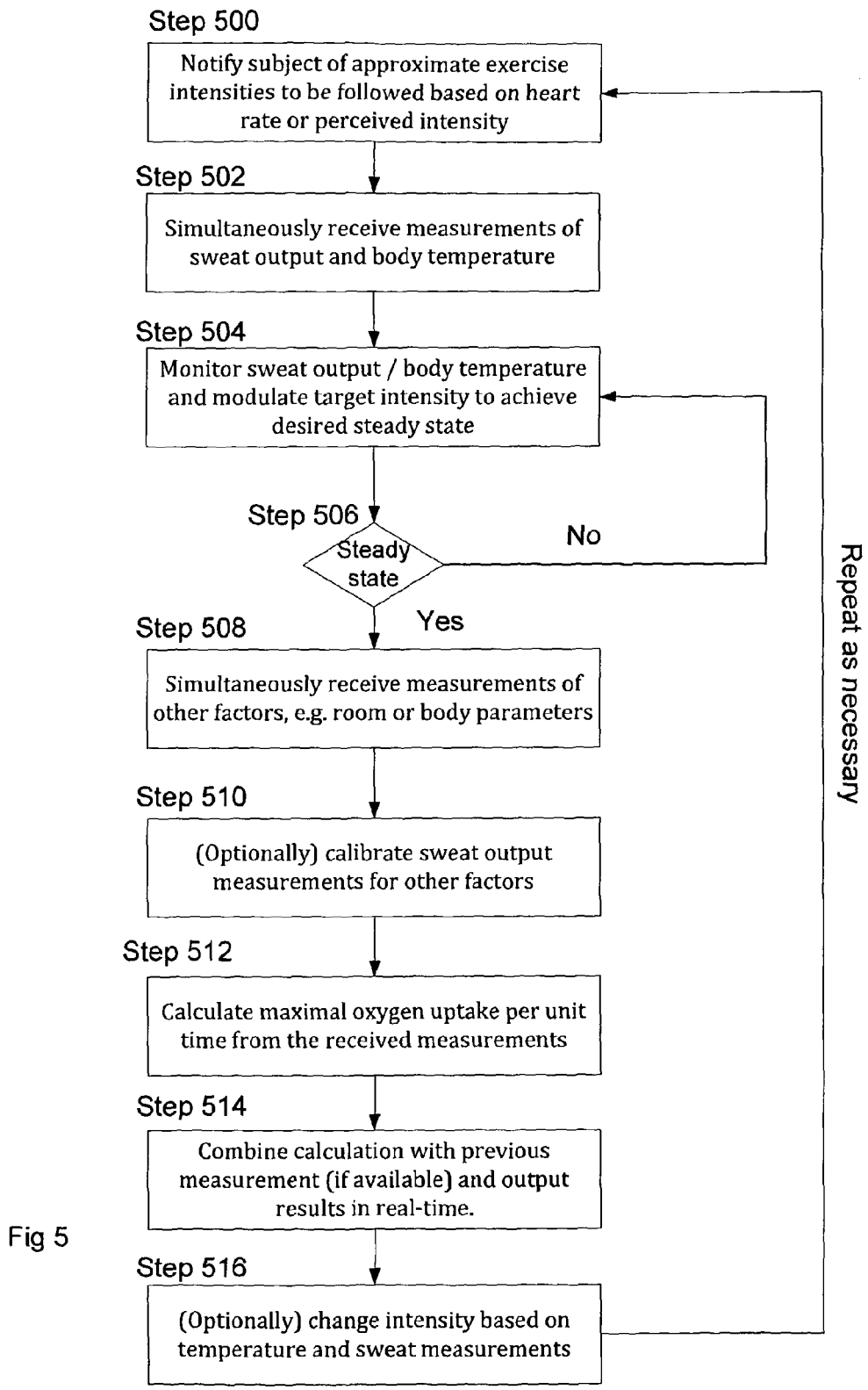
FIG. 5 is a flowchart of the methodology used.

FIG. 5 shows how the relationships above can be used to measure cardiovascular fitness of a subject by calculating maximal oxygen uptake per unit time. The first step 500 is to notify the subject of approximate exercise intensities to be followed based on heart rate or perceived intensity. The notification can be a visual message on the display screen of the interface or computer (of the system shown in FIG. 1) or could be a verbal message. The next step is to simultaneously measure sweat output and body temperature and to send these measurements to the processor. At step 504, the processor determines from these measurements whether or not the subject will attain the desired steady state when working at the original intensity. There are many ways to achieve the desired steady state but it is preferable to achieve steady state as quickly as possible. For example, the subject may initially be subjected to a more intense exercise period which will allow core temperature to be raised rapidly to the desired value. Thereafter, the exercise intensity can be dynamically lowered to rapidly hit steady state.

At step 506, the processor determines whether or not the subject is exercising at steady state. The steady state may be determined by obtaining measurements of body temperature, sweating and other readings, e.g. heart rate or ECG measurements. Alternatively, it may be possible to determine steady-state using whole body measurements, although this is difficult because of sweat on clothing, consumption of fluids, etc. If steady state is not likely to be achieved, the processor will alter the target intensity and this new intensity will be notified to the subject. If the answer is no, the processor repeats step 504 to determine a new intensity level which will result in steady state.

Once at steady state, other measurements of the room parameters or of the subject may also be taken to improve the subsequent calculations (step 508). The original measurements, particularly sweat output, may be calibrated before the final calculation (step 510). The sweat output may be calibrated to allow for variations in environmental conditions, different sweat outputs for different locations, air flow, clothing etc. The calibration may be done by the sensor or the processor.

The measurements are input to the processor to determine the maximal oxygen uptake per unit time from the relationships defined above (step 512). The results of the calculation may be output in real-time as shown in step 514 or may be stored for later analysis. If there are any results from previous tests available, the results may be combined with the new calculations. The overall calculation may be more accurate if the test is repeated at different intensities (both higher and lower). Accordingly, at step 516, there is the option for the processor to automatically set, or a person controlling the test to set, a new intensity level based on the measurements from the previous test. The whole process is then repeated for the new measurements.

$\dot{V}O_2$ max is a measurement which is generally associated with fit healthy people. As identified above, unlike a conventional $\dot{V}O_2$ max test, the proposed test can be conducted on someone with a cardiac or respiratory disorder or a morbidly obese person, provided these individuals can exercise enough to produce a limited sweat. Such a group of people could include post-operative cardiac patients. The test may also be suitable for children. It is possible that the test could be adopted as a mass screening to allow individuals with a genetically high $\dot{V}O_2$ max to be identified early— before they excel at a sport. This could well help identify future high performers.

In the analysis described in relation to FIGS. 4a to 4c, the participants had a restricted range of body mass, heights and age. For example, the average age was approximately 21 (SEM<0.5 for each group), the mass was 54 kg for the females and 64 kg for the males (SEM range 2.1-3.4 for the groups) and height approximately 160 cm for the females and 174 cm for the males (SEM range 1.2-1.8 for the groups). Furthermore, the exercise was done under warm conditions, temperature was measured at multiple points and sweating was assessed with an evaporative technique. The relative homogeneity of the Ichinose-Kuwahara et al. dataset allowed the mean group relationships between sweating and body temperature (males and females of different training status) to be fitted without requiring anthropometric data. This suggested that $\dot{V}O_2$ max might be a simple function of the sweating versus temperature relationship.

Figure 6:
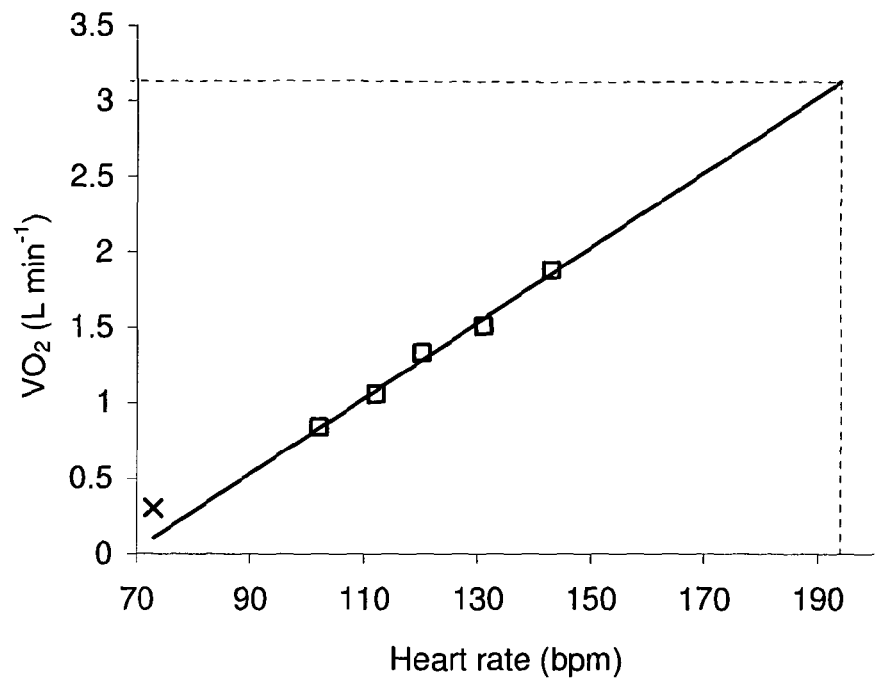
FIG. 6 is a graph showing oxygen consumption per unit time against heart rate for a 26 year old female subject.

As set out in FIG. 5, the calculations for $\dot{V}O_2$ max can be improved by including other data, e.g. information about the subject. FIG. 6 onwards show the results and analysis of another experiment conducted using participants which are on average, older, taller, heavier and cover a much greater age range than the participants for FIGS. 4a to 4c. FIG. 6 onwards show that using anthropometric data in conjunction with the sweating versus temperature relationship allows $\dot{V}O_2$ max prediction from an individual's sweat versus temperature relationship over a wide age range.

Selection for the new trial was based entirely on availability (subject to having no pre-existing health issues that would preclude moderate exercise). Only one participant was refused because he was too heavy for the test equipment. All the subjects gave informed consent and the study was approved by the Human Biology Research Ethics Committee (University of Cambridge). In total 33 subjects (21 male, 12 female) took part in the study and their data is set out below in table 1. Some subjects completed multiple spirometry and sweating tests.

sports. Nevertheless they include a cross-section of the healthy population with an average body mass index approx. 10% below the UK average. The initial dataset included five males with $\dot{V}O_2$ max values >5 L min$^{-1}$, however only two of these met our excess sweat exclusion criterium of <1.22 mg cm$^{-2}$ min$^{-1}$. Three subjects were aged >60 and two aged ≤15. Two subjects (one male, one female) took part in no form of regular aerobic exercise while the remainder ranged from training once a week upwards. Several of the subjects were engaging in an average of >3 hours training per day and competed in endurance sports at international level. We made no systematic attempt to quantify training status beyond this.

Subjects were requested to attend in a normally hydrated state, and with a normal nutritional status, but no other restrictions were placed on prior food intake, exercise or consumption of medications. On arrival the project and associated risks were explained verbally and testing began within approximately 15 mins. No attempt, beyond this procedural delay, was made to allow subjects to reach steady-state with the environment. All experiments were conducted in a well, but passively, ventilated class room (volume 1,468 m$^3$; 20-25° C.) using an exercise bike and for each subject, both the sweating and the spirometry measurements were made in a single visit lasting approximately 1.5 hours. Subjects wore normal sports clothing (T shirt, shorts and sports shoes).

Subjects were fitted with a heart rate monitor (Forerunner 305, Garmin, UK) and instructed how to use the Philips Infrared thermometer by taking a series of 10 measurements whilst at rest. The saddle height was then adjusted to fit. The sweat/spirometry test order was initially random, but later standardized as sweat test followed by spirometry to avoid possible problems of excess sweat production during the spirometry test influencing the sweating test. Since hydration status was not controlled, $\dot{V}O_2$ max values are reported as whole body values (L min$^{-1}$) rather than per unit body mass.

The experiments were performed in a standard large and passively-ventilated laboratory (during the summer months) and participants attended the test sessions in their normal state. These conditions match those that might occur if the

TABLE 1

Participant data

| Mean ± SD (range) | Number | Age Years* | Height M | Mass kg | BMI kg m$^{-2}$ | Spirometry $\dot{V}O_2$ max L min$^{-1}$ |
|---|---|---|---|---|---|---|
| Total | 33 | 31.8 ± 15.4 (14-76) | 1.72 ± 0.11 (1.53-1.94) | 67.0 ± 13.9 (40-95) | 22.5 ± 2.9 (17-27) | 3.62 ± 1.10 (2.22-6.03) |
| Female | 12 | 27.4 ± 9.3 (16-47) | 1.66 ± 0.08 (1.56-1.80) | 58.2 ± 9.3 (47-73) | 21.1 ± 2.9 (17-26) | 2.86 ± 0.47 (2.22-3.59) |
| Male | 21 | 34.2 ± 17.7 (14-76) | 1.75 ± 0.12 (1.53-1.94) | 72.1 ± 13.7 (40-95) | 23.3 ± 2.6 (17-27) | 4.06 ± 1.12 (2.33-6.03) |

Sex, mass and height were either self-reported by the participants, or determined using standard techniques. Values are given as Mean±SD (range). *Age is an underestimate since it was calculated using rounded down integer portion of age rather than birth date. Where a subject conducted more than one Spirometry $\dot{V}O_2$ max test, the mean value was used.

Most of the subjects tested were, or had within the previous 6 months, engaged in some form of endurance sweat-test technique were used 'in the field' to estimate $\dot{V}O_2$ max. However, it is likely that the lack of control will have introduced noise into the dataset. Better control of external temperature, humidity, previous exercise level just prior to the test and hydration status might all further improve the test accuracy. Furthermore, tighter control on exercise intensity may also improve the accuracy further, although the exact way in which this might be implemented without using direct feedback control of the equipment is not clear.

Sweating Test

Subjects were first asked to pedal for 5 mins to achieve approx. 65% of their age-predicted maximum heart rate (220-age) and then to reduce the effort (approx. 50% of their age-predicted heart rate) for a further 19 min period. The heart rate values were not systematically recorded, nor were deviations from the desired rates monitored. No data was discarded on the basis of the heart rates achieved.

During the 19 min period of continuous exercise, five measurements of forearm sweat production were made. Each measurement consisted of a 3 min collection of sweat (with 1 min between collections) from the dorsal surface of the forearm using pre-weighed medical wipes (approx. 0.67 g; 2-ply, folded in half to cover 0.011 $m^2$) surrounded by a single layer of a PVC cling film. Before applying the medical wipe the forearm was wiped dry to remove previously accumulated sweat. Immediately after removal of the medical wipe its increase in mass was determined (0.01 g resolution).

The absorptive sweat collections were made from the dorsal surface of the forearm. No particular attention was paid to the exact location (and the position was not modified by the presence of hair), and timings of collection were made with a stopwatch. Since the measurements were absorptive in nature it is possible that sweat was also collected from neighbouring regions of skin covered by the cling-film but not in direct contact with the tissue. Equally it is also likely that some sweat will have remained on the skin, or have escaped absorption as it flowed between the tissue and the skin. These represent possible errors that may have introduced some noise. Furthermore, skin temperature is known to alter sweat production and the insulative properties of the cling-film and tissue will have caused a gradual rise in skin temperature during the collection period. Accordingly, additional errors may be introduced. It will be appreciated that there are many ways of measuring sweat which may be used.

During the 19 min period the subject also continuously monitored their tympanic temperature (right ear; Braun Thermoscan, resolution 0.1° C.) at a frequency of approx. 0.1 Hz, but, determined by the subject. At the end of the exercise period another 2-3 measurements of sweat production were made, and temperature measurements were continued until sweating ceased.

Since excess sweat production (sweat that does not evaporate) was likely to interfere with the measurements estimates of maximal evaporation rates were made. Evaporation tests from tissue paper, in still air inside a high precision balance (21° C., 50% humidity) suggested a minimum evaporation rate of approx. 0.13 mg $cm^{-1}$ $min^{-1}$. Moving (approx. 0.5 m $s^{-1}$) heated air (approx. 25° C.) increased the evaporation rate to approx. 0.8 mg $cm^{-2}$ $min^{-1}$. Ayling (1986) measured peak sweat evaporation rates of approx. 0.9 mg $cm^{-2}$ $min^{-1}$ during exercise at 32% $\dot{V}O_2$ max and reported that not all sweat produced evaporated. Since our absorptive collection method did not rely on evaporation we were able to use data from higher sweating rates. However, 8 subjects produced excess sweat to the extent that they cooled continuously throughout the test and showed no correlation between body temperature and sweating rate. Data from any test where the maximum sweating rate rose above 1.22 mg $cm^{-2}$ $min^{-1}$ was therefore excluded.

Mean tympanic temperature was calculated for each sweat collection period as the simple numerical average of the values obtained during the period irrespective of changes in the subject-determined sampling rate.

Spirometry Test $\dot{V}O_2$ max was estimated using a simple spirometry extrapolation technique as illustrated in FIG. 6. Briefly, 5 or 6 sets of expired air were collected using Douglas bags (100 L) connected through one-way valves and a mouth piece. The first gas collection period (3 mins) was made with the subject at rest to allow familiarization with the apparatus, and to test the equipment. The data from this period was not used. The subject was then asked to pedal steadily (self-selected cadence with self-selection of resistance) to raise and hold the heart rate at approx. 100 beats per minute. Once the heart rate was judged to be stable (<4 mins of the onset of exercise) gas collection commenced. Gas collection continued until the Douglas bag contained between 50 and 100 L (between 1-3 mins). During the collection period the average heart rate was recorded. Subjects were then requested to raise their heart rates by approx. 10 beats per minute and the collection period was repeated. From measurements of expired volume (Parkinson Cowan gas volume meter), % $O_2$ (ML206, Powerlab 26T, ADInstruments) and collection time $\dot{V}O_2$ max was estimated by extrapolation to an age predicted maximum heart rate (220-age) using linear regression analysis (mean±SD of the coefficient of determination (i.e. the square of the correlation coefficient or $r^2$) for all tests 0.978±0.028, n=56).

Figure 7A:
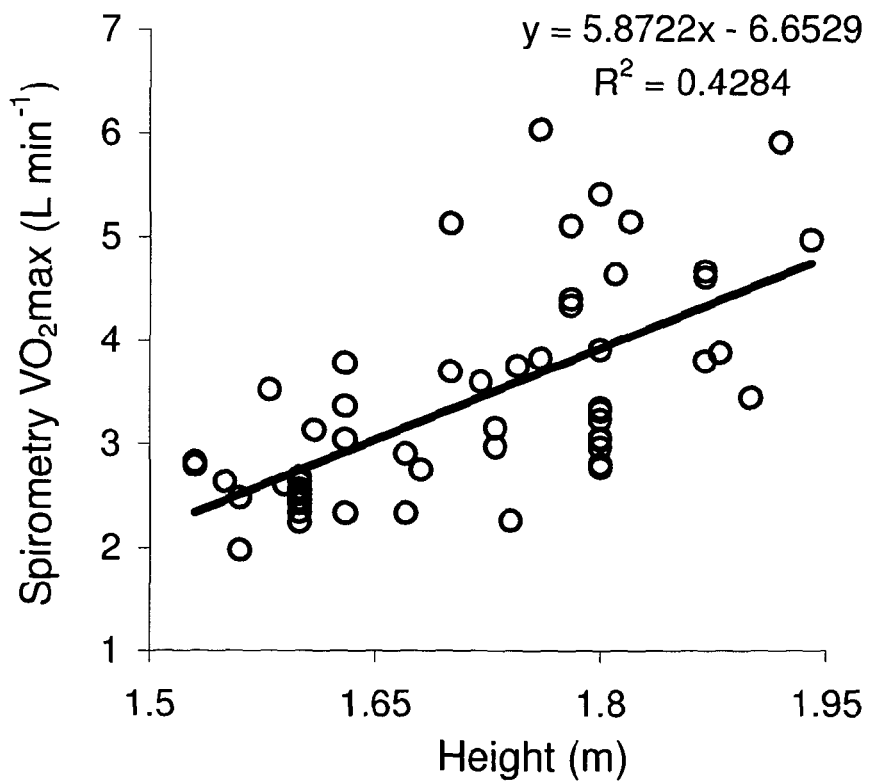
FIGS. 7a and 7b are graphs showing $\dot{V}O_2$ max, estimated from spirometry, plotted against height and age respectively for a test group.
Figures 7B, 7C:
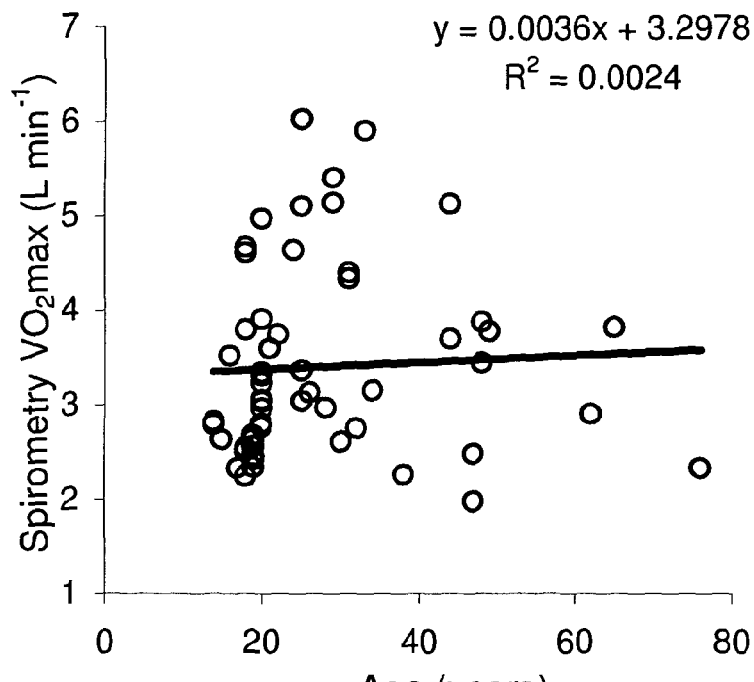
FIG. 7c is a graph showing height plotted against mass.

In FIG. 6, the cross shows the first measurement of oxygen consumption at rest. Five other measurements of oxygen consumption (open squares) were made at increasing heart rates and fitted by least squares (gradient 0.025 L $min^{-1}$ $bpm^{-1}$, offset −1.72 L $min^{-1}$, $r^2$=0.991). An age-predicted maximum heart rate of 194 produces an estimated $\dot{V}O_2$ max of 3.13 L $min^{-1}$ Anthropometric Prediction of $\dot{V}O_2$ Max A total of 56 spirometry tests were conducted; with 9 subjects doing more than one test. For each of these tests, the extrapolated $\dot{V}O_2$ max was plotted against height, and age as shown in FIGS. 7a and 7b, respectively. FIG. 7a shows that the relationship between $\dot{V}O_2$ max and height has the highest correlation and FIG. 7b shows that there is little correlation with age. It is noted that $\dot{V}O_2$ max also correlates with mass (data not shown). FIG. 7c shows that there was also a good correlation between mass and height. In FIG. 7a, the straight line which correlates with the data is defined as y=5.8722x−6.6529, in FIG. 7b, the best fit line is defined as y=0.0036x+3.2978 and in FIG. 7c as y=0.0068x+1.2748. In FIGS. 7a, 7b and 7c, $R^2$ is 0.4284, 0.0024 and 0.7003 respectively.

Figure 7D:
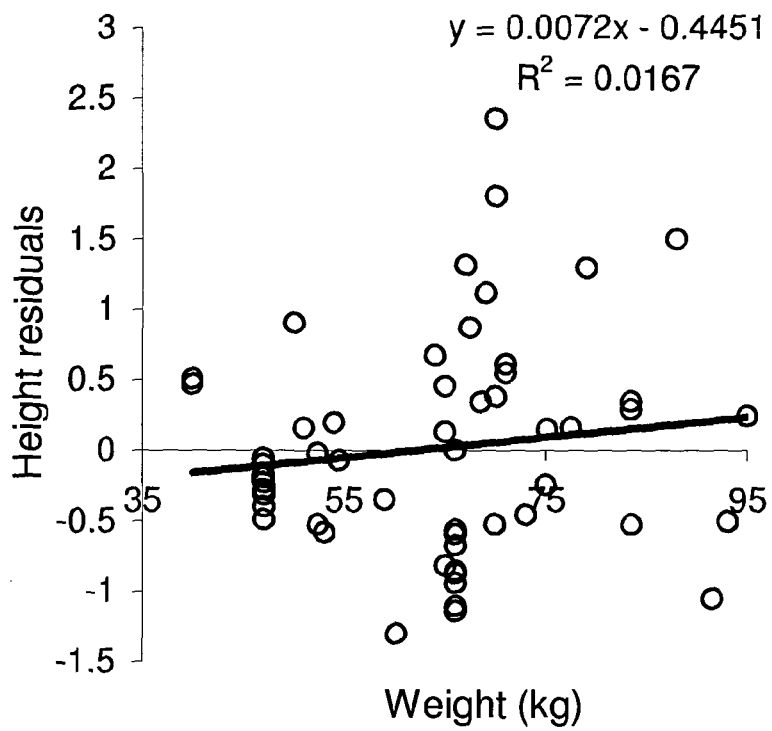
FIG. 7d is a graph showing the residuals from FIG. 7a (the amount of $\dot{V}O_2$ max not predicted by the average relationship) of $\dot{V}O_2$ max from the relationship between $\dot{V}O_2$ max and height, plotted against mass.

FIG. 7d plots the residuals (the amount of $\dot{V}O_2$ max not predicted from the linear relationship between $\dot{V}O_2$ max and height from FIG. 7a) against mass. As shown there is little correlation. The residuals are the absolute amount of the y-variable not accounted for by the average relationship.

Figure 8A:
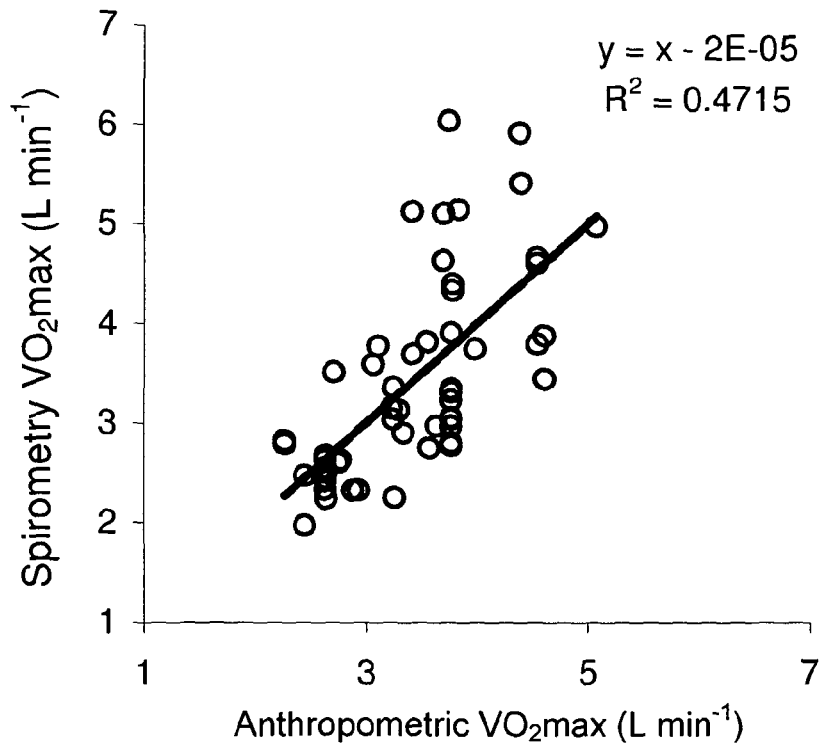
FIG. 8a is a graph of a spirometry prediction of $\dot{V}O_2$ max against an anthropometric prediction of $\dot{V}O_2$ max.
Figure 8B:
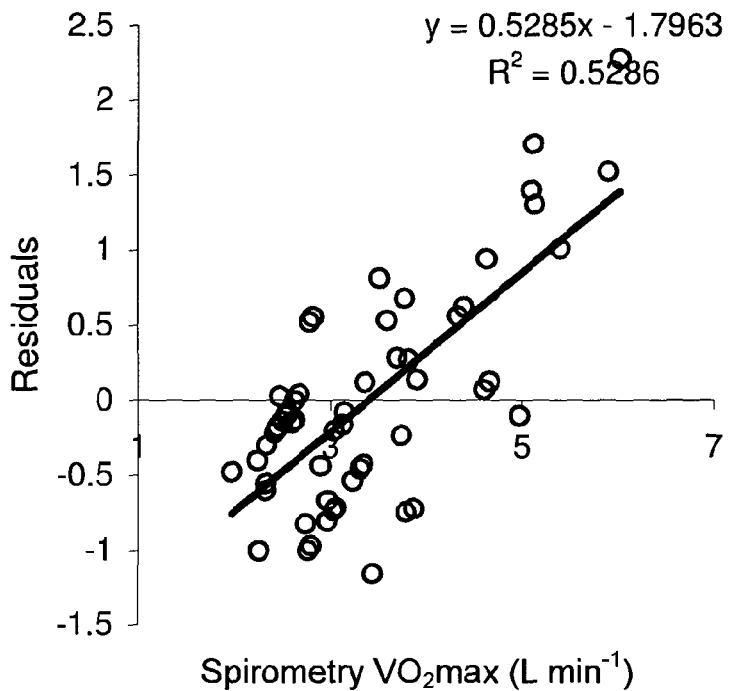
FIG. 8b is a graph of the residuals from FIG. 8a (the amount of spirometry $\dot{V}O_2$ max not predicted by Anthropometric $\dot{V}O_2$ max) against a spirometry prediction of $\dot{V}O_2$ max.

Combining the three anthropometric measurements into a single linear model produced an $r^2$ for all of the tests of 0.47 which is shown in FIG. 8a. As shown in FIG. 8b, the residuals from this relationship had a significant correlation with the spirometry $\dot{V}O_2$ max values. This suggests that the anthropometric model was failing in a systematic fashion. It over predicts individuals with low $\dot{V}O_2$ max and under predicts individuals with high $\dot{V}O_2$ max.

Sweat and Body Temperature Predicted $\dot{V}O_2$ Max

Figure 9A:
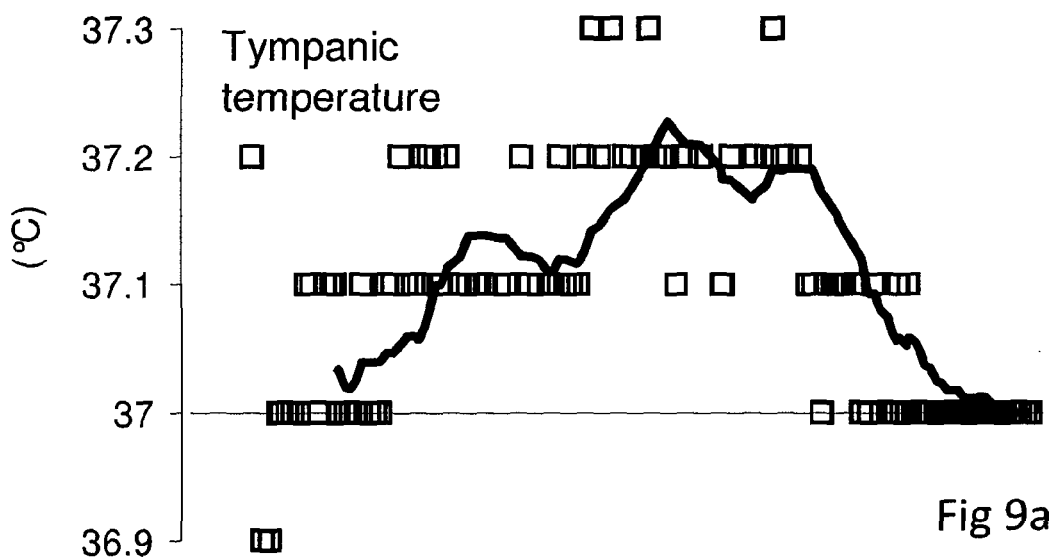
FIGS. 9a and 9b are graphs of tympanic temperature and sweat rate against time for a typical 20 year old male, respectively.
Figure 9B:
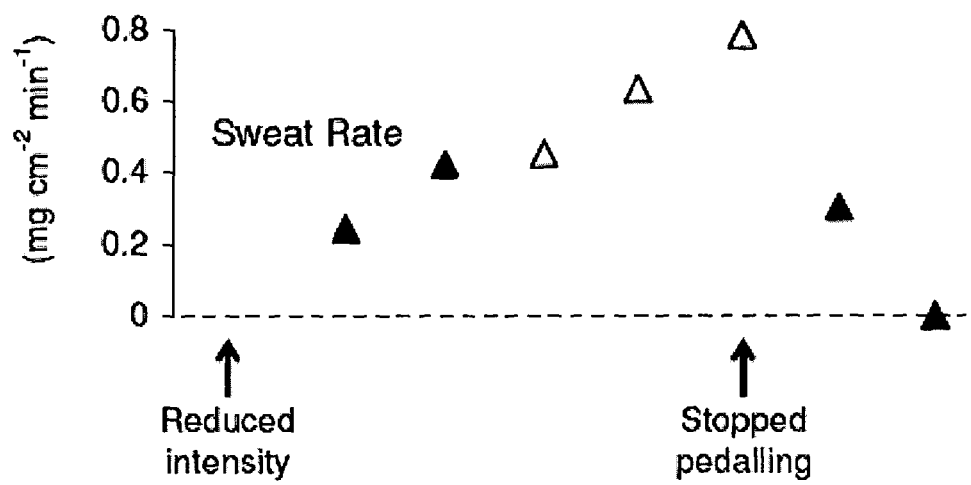
Figure 9C:
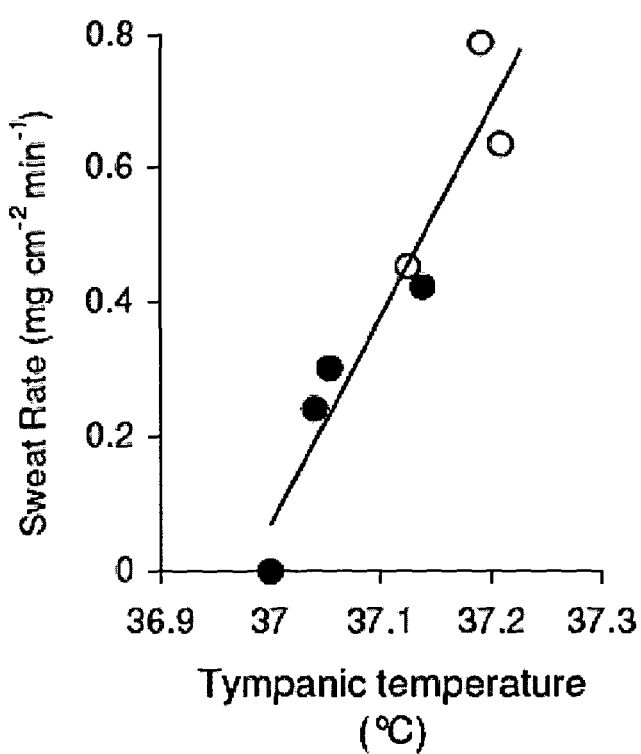

During the sweating tests, several different patterns of body temperature and sweating changes occurred. FIGS. 9a to 9c show an example of the most common pattern. After the 5 min of more intense exercise, the temperature measurements commenced. As shown in FIG. 9a, typically subjects underwent a period of gradual warming approx. 0.3° C. (calculated mean rise). During this time, as shown in FIG. 9b, sweat production also rose. After 19 mins at the lower exercise intensity the subject stopped cycling and tympanic temperature and sweat production fell. Plotting the relationship between sweat production and tympanic temperature as shown in FIG. 9c revealed a close correlation, although a number of subjects showed considerable hysteresis in the relationship. In some subjects the increase in sweat production appeared to precede the tympanic temperature rise whilst in others the reverse occurred.

In FIG. 9a, instantaneous tympanic temperature is plotted as open squares, three minute rolling average of tympanic temperature as a solid line and forearm sweat rate as triangles. In all Figures, exercise began 5 mins before the start of the trace. At the first arrow shown below FIG. 9b, the subject reduced the exercise intensity from approx. 130 bpm to approx. 100 bpm. At the second arrow the subject ceased exercise. The open triangles in FIG. 9b show the $3^{rd}$, $4^{th}$ & $5^{th}$ sweat collections that were used for subsequent analysis.

FIG. 9c is a plot of sweat rate against tympanic temperature taken from FIGS. 9a and 9b fitted by least squares (sweat rate=3.1*tympanic temperature-115; $r^2$=0.901). The temperature values are the simple mean of the reading taken during the period of sweat collection. The open circles show data used for subsequent analysis. ($3^{rd}$, $4^{th}$ and $5^{th}$ measurements).

In some of the subjects a rather different relationship between sweat production and tympanic temperature occurred and the reduction of exercise intensity at the end of the 5 min period was followed by a period of cooling. These subjects were not analyzed further and were all excluded by the excess sweat criterium.

Figure 10A:
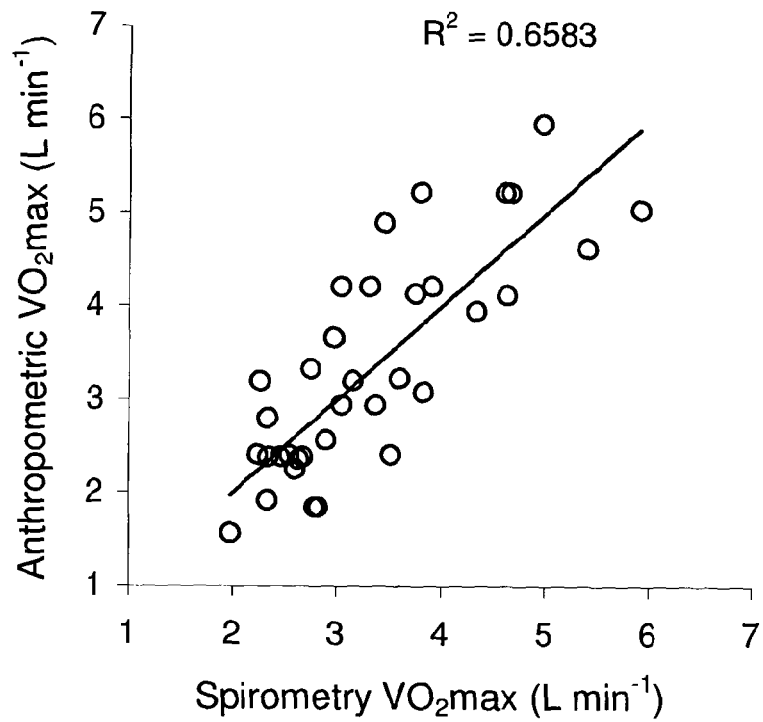
FIGS. 10a and 10b are graphs plotting an anthropometric prediction of $\dot{V}O_2$ max and a sweat and anthropometric-derived prediction of $\dot{V}O_2$ max against a spirometry prediction of $\dot{V}O_2$ max.

For the remaining subjects (n=37 tests from 26 individuals) an anthropometric estimation of $\dot{V}O_2$ max was made and plotted against the spirometric value as shown in FIG. 10a. The anthropometric estimated $\dot{V}O_2$ max was calculated using the linear equation $$\dot{V}O_2\text{max} = a \times \text{height} + b \times \text{weight} - c \times \text{age} - d$$

The constants a=2.83, b=0.013, c=0.011 and d=5.89 (with height in m, weight in kg, age in years) were determined by a standard iterative least squares fit of the anthropometric $\dot{V}O_2$ max to the spirometry $\dot{V}O_2$ max. Since this dataset had excluded some high $\dot{V}O_2$ max individuals ($\dot{V}O_2$ max 4.58±1.10 L min$^{-1}$, mean±SD, n=8), the fit was better, namely $r^2$=0.6583 for 37 measurements.

The model (linear equation above) was then augmented by an additional term containing both temperature and sweat as set out in the equation below $$\dot{V}O_2\text{max} = \frac{e \times \text{Sweat}^{2.18}}{(\text{temp} - f)} - a \times \text{age} + b \times \text{height} + c \times \text{weight} - d$$

Figure 10B:
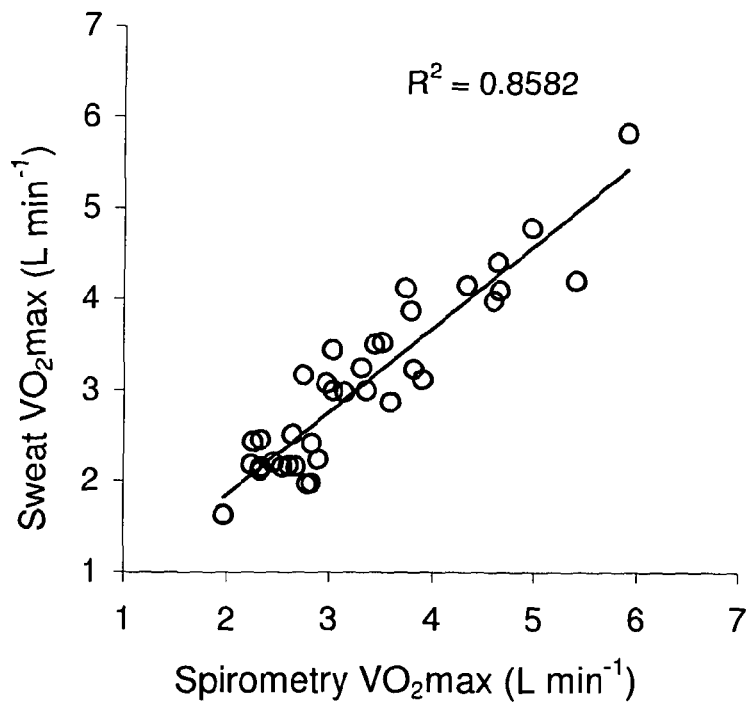

The constants a=0.0288, b=0.383, c=0.0477, d=0.0147, e=2.97 and f=35.03 were determined by an iterative least squares fit of the anthropometric $\dot{V}O_2$ max to the spirometry $\dot{V}O_2$ max. It will be appreciated that the power to which sweat is raised may also be a constant g which is determined along side the other parameters. It is noted that parameters a to d are different from the corresponding parameters in the linear relationship, which does not include temperature and sweat. As shown in FIG. 10b, the plot of this anthropometric $\dot{V}O_2$ max to the spirometry $\dot{V}O_2$ max produced a significantly better fit ($r^2$ approximately 0.86). The prediction is not perfect, and there are some outliers. Nevertheless, the predictive ability of the sweating data (combined with anthropometric data) is considerably better than can be achieved with anthropometric data alone and probably as good as can be expected given that repeated spirometry-based tests $\dot{V}O_2$ max vary in a similar fashion.

Using anthropometric data alone increases the potential for failure with individuals with very similar anthropometric data (e.g. University rowers). By contrast, including data from the sweat test should improve results. For example, the sweat test may be very sensitive to training and a good way to track the cumulative effects of training. In essence, anthropometric data may provide a bench mark $\dot{V}O_2$ max to start from and training alters the sweat temperature and refines the value.

FIG. 11 also illustrates that the anthropometric only estimation technique is greatly improved using the sweating data. Considering firstly a group of three females spanning a reasonably large age range; two of them (AS & GS), both small (one young, one old) are predicted by anthropometric-only data to have lower $\dot{V}O_2$ max than their spirometry measurements. In both cases the inclusion of the sweating data greatly improves the prediction. KS is included by way of an example of how anthropometric-only prediction can yield the correct value and the further inclusion of the sweating data does not cause any major errors.

The next example is of two males who span the full age range. In both cases the anthropometric-only prediction is too low and the inclusion of the sweating data vastly improves the prediction. Finally, there is a group of four tall and heavier males. In three cases the anthropometric-only prediction over-estimates $\dot{V}O_2$ max and in the other case it under-estimates. In all cases the inclusion of the sweating data improves the estimation.

For both the anthropometric prediction and the sweating prediction the equations were derived from the best fit to the entire set of subject tested. The subjects shown here are a selection of those for whom the anthropometric prediction was particularly poor (except KS who is included to demonstrate that inclusion of the sweating data does not reduce the quality of the estimation).

The refined equation above is in line with the original concept of FIG. 5 in which sweat and temperature are used as the primary indicators of $\dot{V}O_2$ max with body parameters, namely the anthropometric data, e.g. height, weight (mass) and age, being included to optimise the results. In summary, FIG. 6 onwards show:

1. Sweating and temperature measurements can refine anthropometric prediction of $\dot{V}O_2$ max (or phrased another way, that anthropometric prediction can refine sweating and temperature measurement prediction). In other words, a technique using a combination of anthropometric sweating and temperature measurement prediction of $\dot{V}O_2$ max produces the best results.
2. The combination technique does not require (although it will benefit from) tight control of environmental conditions and can be extended to a wider age range.
3. There are limitations to the combination technique including maximal sweating rates and maximal exercise intensities beyond which the relationship appears to breakdown.
4. The equation predicting $\dot{V}O_2$ max which utilizes both sweating and temperature data is of a different form at lower temperatures and when including anthropometric data.
5. The equation predicting $\dot{V}O_2$ max using both sweating and temperature data may, in some cases, over estimate $\dot{V}O_2$ max in individuals engaged in intense training programs.

6. It was observed that in some sedentary individuals not undergoing any form of training sweating rates (and $\dot{V}O_2$ max) were very low. This is potentially an important way of identifying individuals who may benefit from more intense exercise.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. An apparatus for determining an index of cardiovascular fitness for a subject, the apparatus comprising:
    body sensors including:
        at least one temperature sensor configured to measure a body temperature of the subject;
        at least one sweat output sensor configured to measure a sweat output of the subject; and
        a heart rate sensor configured to measure a heart rate of the subject;
    a display;
    a processor in communication with the body sensors and the display, the processor configured to:
        display a target heart rate via the display;
        collect the body temperature, the sweat output and the heart rate from said body sensors in real time;
        determine whether or not the body temperature, the sweat output, or the heart rate indicate that said subject is exercising in steady state at an exercise intensity that is below a maximum exercise intensity for the subject, and
        adjust the target heart rate on the display until the steady state is reached; and
        calculate, at said steady state, the index of cardiovascular fitness for said subject, the index including a maximal oxygen uptake rate of the subject, from:

$$\dot{V}O_2\text{max} = \ln\left(\frac{S}{a}\right) \times \frac{c}{M \times (T-b)},$$

where $\dot{V}O_2$ max is the maximal oxygen uptake rate of the subject per unit body mass, S is the sweat output of the subject, M is the body mass of the subject, T is the body temperature of the subject and a, b, c are predetermined regression constants from empirical data;
    wherein the processor is further configured to display the index via the display.

2. The apparatus according to claim 1, further comprising at least one room sensor configured to measure parameters of a room in which the subject is exercising.

3. The apparatus according to claim 2, wherein said processor is configured to receive measurements from said at least one room sensor and to refine the determination of said subject is exercising in steady state based on the measurements received from the at least one room sensor.

4. The apparatus according to claim 2, wherein said processor is configured to calibrate one or more measurements from at least one of the body sensors based on the measurements from said at least one room sensor.

5. The apparatus according to claim 1, wherein the at least one temperature sensor configured to measure the body temperature of the subject comprises at least one sensor configured to measure skin temperature and at least one sensor configured to measure core temperature.

6. The apparatus according to claim 1, wherein the at least one sweat output sensor configured to measure the sweat output is in the form of a sleeve.

7. The apparatus according to claim 1, wherein S is normalized per sweat gland.

8. The apparatus according to 7, wherein the processor is further configured to:
    determine the constants from measurements taken during exercising of subjects with known maximal oxygen uptake.

9. The apparatus according to claim 1, wherein the processor is further configured to:
    receive body parameter data for the subject and to include said body parameter data in calculating the index of cardiovascular fitness.

10. The apparatus according to claim 9, wherein the body parameter data includes age, height and weight of the subject.

* * * * *